United States Patent
Vogt et al.

(10) Patent No.: US 10,987,147 B2
(45) Date of Patent: Apr. 27, 2021

(54) BONE CEMENT APPLICATOR WITH HOLLOW CYLINDER ON DELIVERY PLUNGER

(71) Applicant: Heraeus Medical GmbH, Wehrheim (DE)

(72) Inventors: Sebastian Vogt, Erfurt (DE); Thomas Kluge, Vallendar (DE); Rainer Strathausen, Friedrichsdorf (DE)

(73) Assignee: Heraeus Medical GmbH, Wehrheim (DE)

( * ) Notice: Subject to any disclaimer, the term of this patent is extended or adjusted under 35 U.S.C. 154(b) by 248 days.

(21) Appl. No.: 15/981,319

(22) Filed: May 16, 2018

(65) Prior Publication Data

US 2018/0333176 A1    Nov. 22, 2018

(30) Foreign Application Priority Data

May 17, 2017   (DE) ..................... 10 2017 110 732.0

(51) Int. Cl.
*A61B 17/88*     (2006.01)
*B01F 15/02*    (2006.01)
(Continued)

(52) U.S. Cl.
CPC ...... *A61B 17/8833* (2013.01); *A61B 17/8822* (2013.01); *A61B 17/8825* (2013.01);
(Continued)

(58) Field of Classification Search
CPC .............. A61B 7/8833; A61B 17/8838; A61B 17/8802; A61B 17/8805; A61B 17/8822; A61B 17/8825; A61B 17/8827
See application file for complete search history.

(56) References Cited

U.S. PATENT DOCUMENTS

| 2,446,501 A | 8/1948 | Weber |
| 3,739,947 A | 6/1973 | Baumann et al. |
(Continued)

FOREIGN PATENT DOCUMENTS

| CN | 102574624 | 7/2012 |
| CN | 103318551 | 9/2013 |
(Continued)

OTHER PUBLICATIONS

Kühn, Klaus-Dieter, "Bone Cements," Springer-Verlag, pp. 9 (2000).
(Continued)

*Primary Examiner* — Matthew J Lawson
(74) *Attorney, Agent, or Firm* — Dicke, Billig & Czaja, PLLC

(57) ABSTRACT

One aspect relates to a device for producing a bone cement paste from a monomer liquid and a cement powder as parent components of the bone cement paste and for delivering the mixed bone cement paste. The device has a cartridge with a cylindrical interior. The interior of the cartridge is closed at a front side apart from a delivery opening for discharging the bone cement paste. In the interior of the cartridge a delivery plunger is arranged which is pushable in the direction of the delivery opening. The cement powder is arranged in the interior of the cartridge between the delivery opening and the delivery plunger. A hollow cylinder is arranged at a front side of the delivery plunger facing the delivery opening. The hollow cylinder is open at its front face facing the delivery opening and extends from the front side of the delivery plunger at least 3 mm into the interior of the cartridge.

21 Claims, 9 Drawing Sheets

(51) Int. Cl.
*B01F 13/00* (2006.01)
*A61B 17/00* (2006.01)

(52) U.S. Cl.
CPC ...... *A61B 17/8827* (2013.01); *B01F 13/0023* (2013.01); *B01F 15/0206* (2013.01); *B01F 15/0237* (2013.01); *B01F 15/0279* (2013.01); *A61B 2017/00477* (2013.01); *A61B 2017/00955* (2013.01); *A61B 2017/8838* (2013.01); *B01F 2215/0029* (2013.01)

(56) References Cited

U.S. PATENT DOCUMENTS

| | | | | |
|---|---|---|---|---|
| 3,756,390 | A * | 9/1973 | Abbey | A61M 5/284 206/219 |
| 3,785,379 | A * | 1/1974 | Cohen | A61M 5/31596 604/88 |
| 4,055,177 | A * | 10/1977 | Cohen | A61M 5/31596 604/88 |
| 4,671,263 | A | 6/1987 | Draenert | |
| 4,758,096 | A | 7/1988 | Gunnarsson | |
| 4,973,168 | A | 11/1990 | Chan | |
| 5,100,241 | A | 3/1992 | Chan | |
| 5,344,232 | A | 9/1994 | Nelson et al. | |
| 5,586,821 | A | 12/1996 | Bonitati et al. | |
| 5,588,745 | A | 12/1996 | Tanaka et al. | |
| 5,624,184 | A | 4/1997 | Chan | |
| 5,997,544 | A | 12/1999 | Nies et al. | |
| 6,033,105 | A | 3/2000 | Barker et al. | |
| 6,709,149 | B1 | 3/2004 | Tepic | |
| 6,935,541 | B1 | 8/2005 | Campbell et al. | |
| 2004/0074927 | A1 | 4/2004 | Lafond | |
| 2008/0312588 | A1 * | 12/2008 | Faccioli | B01F 15/0205 604/87 |
| 2009/0234363 | A1 | 9/2009 | Booth, III et al. | |
| 2011/0056984 | A1 | 3/2011 | Cheetham | |
| 2012/0155214 | A1 * | 6/2012 | Faccioli | A61B 17/8825 366/130 |
| 2013/0035664 | A1 * | 2/2013 | Mojdehbakhsh | A61M 5/3234 604/506 |

FOREIGN PATENT DOCUMENTS

| | | |
|---|---|---|
| DE | 2838222 | 3/1980 |
| DE | 3640279 | 6/1987 |
| DE | 69812726 | 2/2004 |
| DE | 202005010206 | 10/2005 |
| DE | 102009031178 | 9/2010 |
| EP | 0112574 | 7/1984 |
| EP | 0692229 | 1/1996 |
| EP | 0796653 | 9/1997 |
| EP | 1005901 | 6/2000 |
| EP | 1016452 | 7/2000 |
| EP | 1020167 | 7/2000 |
| EP | 1886647 | 2/2008 |
| EP | 2457531 | 5/2012 |
| WO | 9426403 | 11/1994 |
| WO | 9967015 | 12/1999 |
| WO | 0035506 | 6/2000 |
| WO | 2011089480 | 7/2011 |
| WO | 2014205063 | 12/2014 |
| WO | 2016/014764 | 1/2016 |

OTHER PUBLICATIONS

Charnley, J., "Anchorage of the Femoral Head Prosthesis of the Shaft of the Femur," The Journal of Bone and Joint Surgery, 42 B, No. 1, pp. 28-30 (Feb. 1960).

* cited by examiner

BONE CEMENT APPLICATOR WITH HOLLOW CYLINDER ON DELIVERY PLUNGER

CROSS-REFERENCE TO RELATED APPLICATION

This Utility Patent Applications claims priority to Patent Application No. DE 10 2017 110 732.0, filed on May 17, 2017, which is incorporated herein by reference.

BACKGROUND

One embodiment relates to a device for producing a bone cement paste from a monomer liquid and a cement powder as parent components of the bone cement paste and for delivering the mixed bone cement paste. One embodiment also relates to a method for producing a bone cement paste, for example, a pasty polymethyl methacrylate bone cement paste, using such a device.

One embodiment, for example, provides a device for separate storage of the cement powder and of the monomer liquid of polymethyl methacrylate bone cement, for subsequent mixing of the cement powder with the monomer liquid to form a bone cement paste and for delivery of the mixed bone cement paste. The device according to one embodiment is in one embodiment a full-prepacked cementing system.

Polymethyl methacrylate (PMMA) bone cements are attributed to the pioneering work carried out by Sir John Charnley (Charnley, J.: Anchorage of the femoral head prosthesis of the shaft of the femur. J. Bone Joint Surg. 42 (1960) 28-30). Conventional polymethyl methacrylate (PMMA) bone cements are composed of a pulverulent component and a liquid monomer component (K.-D. Kühn: Knochenzemente für die Endoprothetik: Ein aktueller Vergleich der physikalischen und chemischen Eigenschaften handelsüblicher PMMA-Zemente [Bone Cements for Endoprosthetics: An Up-To-Date Comparison of the Physical and Chemical Properties of Commercial PMMA Cements]. Springer-Verlag Berlin Heidelberg New York 2001). The monomer component in general contains the monomer methyl methacrylate and an activator dissolved therein (N,N-dimethyl-p-toluidine). The powder component, also known as cement powder or bone cement powder, includes one or more polymers which are produced on the basis of methyl methacrylate and comonomers, such as styrene, methyl acrylate or similar monomers by polymerization, for example, suspension polymerization, an x-ray opaque material and the initiator dibenzoyl peroxide. Mixing of the powder component with the monomer component results, through swelling of the polymers of the powder component in the methyl methacrylate, in a plastically deformable paste, the bone cement or bone cement paste proper. On mixing of the powder component with the monomer component, the activator N,N-dimethyl-p-toluidine reacts with dibenzoyl peroxide to form free radicals. The free radicals formed initiate free-radical polymerization of the methyl methacrylate. As polymerization of the methyl methacrylate proceeds, the viscosity of the bone cement paste increases, until it solidifies.

PMMA bone cements may be mixed in suitable mixing cups using spatulas by mixing the cement powder with the monomer liquid. This may result in air bubbles being entrapped in the bone cement paste, which may have a negative effect on the mechanical properties of the cured bone cement.

To avoid entrapped air in the bone cement paste, a wide range of vacuum cementing systems have been described, of which the following are stated by way of example: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, EP 1 886 647 A1, U.S. Pat. No. 5,344,232 A.

A further development in cementing technology is represented by cementing systems in which both the cement powder and the monomer liquid have already been packed in separate compartments of the mixing devices and are mixed together in the cementing system only immediately before application of the cement. Such closed, full-prepacked mixing devices have been proposed in EP 0 692 229 A1, DE 10 2009 031 178 B3, U.S. Pat. Nos. 5,997,544 A, 6,709,149 B1, DE 698 12 726 T2, EP 0 796 653 A2 and U.S. Pat. No. 5,588,745 A.

Patent DE 10 2009 031 178 B3 discloses a storage and mixing device in the form of a full-prepacked cementing system, in which the parent components needed to produce the bone cement paste have already been stored in the storage and mixing device and may be combined and mixed in the storage and mixing device. The storage and mixing device has a two-part delivery plunger for closing a cement cartridge. In this case, a combination of a gas-permeable sterilization plunger and a gas-impermeable sealing plunger is used.

After mixing of the cement powder with the liquid monomer component, polymethyl methacrylate bone cements are applied as bone cement paste in the as yet uncured, pasty state. When using mixing devices, in the case of powder/liquid cements the bone cement paste is located in a cartridge. When applying such conventional PMMA bone cements, after mixing of the two parent components the bone cement paste formed is expelled using manually operable expulsion devices. The bone cement paste is pushed out of the cartridge through the movement of a delivery plunger. Delivery plungers conventionally have a diameter of between 30 mm and 40 mm and thus a surface area on the outside, against which a tappet or a rod of the expulsion device acts during the expulsion process, of 7.0 $cm^2$ to 12.5 $cm^2$. Movement of the delivery plunger is, for example, brought about by manually operable, mechanical expulsion devices. These manual expulsion devices normally achieve an expulsion force in the range of around 1.5 kN to 3.5 N.

These simple mechanical expulsion devices, for example, use clamping rods for expulsion purposes, these being driven by a manually actuatable rocker arm. Manually driven expulsion devices have been tried and tested for decades throughout the world and constitute the existing state of the art. One advantage of these expulsion devices is that, by way of the manual force to be applied, the medical user gains a feel for the bone cement paste's resistance to penetration into the bone structures (cancellous bone).

When using any of the hitherto known full-prepacked cementing systems, the medical user has to perform a plurality of working steps in a predetermined order on the devices in succession until the mixed bone cement paste is obtained and can be applied. Any mistakes in the working steps may lead to failure of the mixing device and therefore cause disruption to the course of the operation. Costly training of medical users is therefore necessary, to avoid user error.

WO 00/35506 A1 proposes a device in which polymethyl methacrylate cement powder is stored in a cartridge, wherein the cement powder fills the entire volume of the cartridge and the interspaces between the particles of the cement powder have a volume which corresponds to the volume of monomer liquid necessary to produce bone cement paste with the cement powder stored in the cartridge. This device is constructed such that, through the action of a vacuum, the monomer liquid is introduced from above into the cartridge, wherein to this end a vacuum is applied to a vacuum port at the bottom of the cartridge. In this way, the monomer liquid is drawn through the cement powder, wherein the air located in the interspaces between the cement powder particles is displaced by the monomer liquid. Thorough mechanical mixing with a stirrer of the cement paste formed is thus dispensed with.

One disadvantage of this system is that cement powders which swell rapidly with the monomer liquid cannot be mixed using this device, because the rapidly swelling cement powder particles form a gel-like barrier once the monomer liquid has penetrated by roughly 1 to 2 cm into the cement powder and prevent migration of the monomer liquid throughout the cement powder. Conventional cement powders additionally suffer from the phenomenon that, due to different surface energies, the cement powder particles are only poorly wetted by methyl methacrylate. The methyl methacrylate thereby penetrates only relatively slowly into the cement powder. Furthermore, the risk cannot be ruled out of the monomer liquid being sucked off via the vacuum port under the action of the vacuum once the cement powder has penetrated fully through the monomer liquid. Then insufficient monomer liquid is available for curing by free-radical polymerization or the mixing ratio is modified undesirably and thus also the consistency of the bone cement paste. It is moreover a problem that the air enclosed between the cement powder particles has to be displaced from the top downwards through the monomer liquid, because the air, which is of a lower specific weight than the monomer liquid, has the tendency, due to gravity, to migrate upwards in the cement powder and not to migrate downwards in the direction of the vacuum port.

Electrically driven expulsion devices are also known from the field of adhesives and sealants. These apparatuses may be driven both with primary and secondary cells and also by means of a stationary power supply. With their sometimes very significant expulsion forces, these devices may expel particularly viscous, pasty compositions. One disadvantage of the use of electric motors, however, is that they contain non-ferrous metals and are costly to purchase. In the operating area, which must be kept sterile, such devices have to undergo complex sterilization or even be replaced. Electrical wiring may impede movement of the user while operating.

Pneumatic devices have moreover also been proposed. These apparatuses require a stationary or mobile compressed air connection (U.S. Pat. No. 2,446,501 A, DE 20 2005 010 206 U1). To this end, compressed air hoses are needed, which may impede the user's movement.

It is alternatively also possible to use compressed gas cartridges to provide compressed gas. To this end, devices have been proposed in which the compressed gas inflow is controlled by one valve, with the flow of viscous composition being additionally controlled by a second valve (US 2004/0074927 A1, U.S. Pat. No. 6,935,541 B1). In the case of these devices, the gas cartridges are integrated into the devices. In such systems connected to compressed air or containing compressed gas cartridges, a compressed gas source is always necessary, the systems no longer being usable without such a source.

For these and other reasons, a need exists for the present embodiments.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
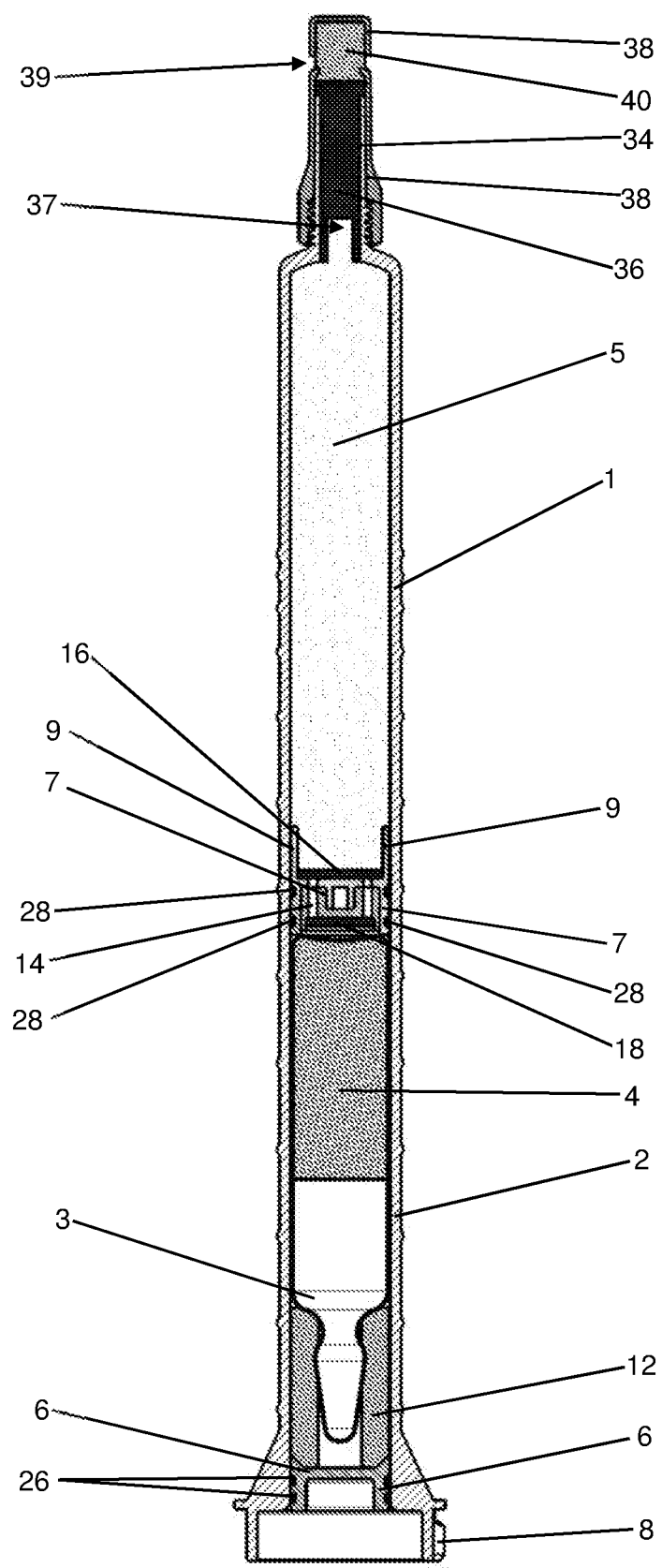
FIG. 1 illustrates a schematic cross-sectional view of an exemplary device according to one embodiment for storing and mixing a monomer liquid and a cement powder.

In the following Detailed Description, reference is made to the accompanying drawings, which form a part hereof, and in which is illustrated by way of illustration specific embodiments in which one embodiments may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present embodiments. The following detailed description, therefore, is not to be taken in a limiting sense, and the scope of the present embodiments are defined by the appended claims.

It is to be understood that the features of the various exemplary embodiments described herein may be combined with each other, unless specifically noted otherwise.

DE 10 2016 121 607, which is not a prior publication, proposes a full-prepacked cementing system with a cartridge containing a bone cement powder. A delivery plunger is provided in the cartridge and behind the cartridge a receptacle is arranged containing a monomer liquid container. At the back side of the receptacle there is located a conveying plunger, with which the monomer liquid container may be squashed and the monomer liquid may be forced out of the receptacle into the cartridge.

Practical tests have illustrated that the bone cement paste produced using this device always has a good consistency if a suitable cement powder and a suitable ratio by weight of cement powder to monomer liquid are used. If the burst monomer liquid container is maximally compressed during monomer transfer, then a good cement paste is reproducibly obtained. However, certain combinations may lead to an undesirable change in the consistency of the bone cement paste at the end of the expulsion process, the mixing ratio between the cement powder and the monomer liquid having been changed. In the volumetric range of a few microliters, one to a few small monomer bubbles may however also sometimes occur at the edge of the expelled cement paste.

For the purposes of at least one embodiment, it has been found that this is associated with the selection and stability of the monomer liquid container and with the penetration of the monomer liquid between the cement powder and an internal wall of the cartridge. Under incomplete compression of the burst monomer liquid container, which may arise for example through selection of a monomer liquid container with very robust walls, a remnant of the monomer liquid may namely remain between the delivery plunger and the conveying plunger within the fragments of the split monomer liquid container, which remnant may exit through the delivery pipe at the end of expulsion of the bone cement paste through subsequent continued compression of the split monomer liquid container as a result of axial movement of the conveying plunger towards the delivery plunger. The monomer liquid may creep between the cement powder and the internal wall of the cartridge along the internal wall of the cartridge, without mixing quickly together with surrounding cement powder in the process.

Various embodiments thus consists in overcoming the disadvantages of the prior art. For example, one embodiment consists in developing a device which is provided and suitable for mixing the bone cement paste from the parent components and for delivering the mixed bone cement paste, and a method for producing a bone cement paste, for example, a pasty polymethyl methacrylate bone cement paste, wherein the bone cement paste is produced from a cement powder and a monomer liquid using such a device, which device and method overcome the disadvantages of the previous devices and methods. One embodiment prevents the formation of monomer bubbles in the bone cement paste produced. Furthermore, one embodiment improves such a device in such a way that the monomer liquid is actively prevented from exiting from the delivery pipe of the cartridge at the end of delivery of the bone cement paste even in the event of incomplete compression of the monomer liquid container. With the device according to one embodiment and the method according to one embodiment it is thus intended to ensure that, even with a very simple and inexpensive device structure and at the same time with very simple and uncomplicated device usability from start to finish of the expulsion process, a homogeneous bone cement paste may be produced and applied. The object is therefore to improve the device described DE 10 2016 121 607, which is not a prior publication, in such a way that formation of the bone cement paste is reproducibly possible without the stochastic occurrence of small amounts of entrapped monomer in the bone cement paste.

The device is intended to be drivable by a simple expulsion device and in the process to be as simple as possible to operate. The structure is intended to be inexpensive, and thus the device can only be used once for reasons of hygiene. Many or all of the processes proceeding in the device, such as mixing of the parent components, delivery of the bone cement paste and optionally also opening of the monomer liquid container and optionally also opening of the cartridge are intended to proceed with the smallest possible number of working steps and as far as possible automatically and in one embodiment to be driven with a single linear drive.

One embodiment thus also consists in the development of a device for mixing cement powder and monomer liquid. Handling of the device is intended to be maximally simplified, in order fundamentally to avoid user error as a result of assembly steps performed incorrectly. The intention is for a medical user to connect the device to an expulsion device after removal from packaging and then to actuate the latter device. It is intended to avoid further assembly and working steps by the structure of the device. The device is intended in one embodiment also to enable safe storage of cement powder and monomer liquid in mutually isolated compartments, so as to rule out unintentional mixing of the cement components during storage of the device. The device is intended to allow sterilization with the gas ethylene oxide. To this end, the cement powder stored in the device must be accessible to ethylene oxide. The device is intended to be activatable by means of an expulsion device driven manually during surgery, such that, after interlocking or frictional connection of the device to the expulsion device, through actuation of the expulsion device the axially advanceable rod of the expulsion device acts on the device, optionally opens the monomer liquid container and then, on further movement of the rod, transfers the monomer liquid into the cement powder. Mixing of the monomer liquid with the cement powder is intended to proceed without a mixer movable manually from outside. It is intended, as far as possible, for mixing of the cement components with formation of the bone cement paste and expulsion of the mixed bone cement paste to proceed only with the forward movement of the rod of the expulsion device. One embodiment is also intended for opening of the monomer liquid container and subsequent monomer liquid transfer into the cement powder to proceed as far as possible only with the forward movement of the rod of the expulsion device.

One embodiment is a device for producing a bone cement paste from a monomer liquid and a cement powder as parent components of the bone cement paste and for delivering the mixed bone cement paste, the device having a cartridge with a cylindrical interior, wherein the interior of the cartridge is closed at a front side apart from a delivery opening for discharging the bone cement paste, wherein a delivery plunger is arranged in the interior of the cartridge the delivery plunger being pushable in the direction of the delivery opening and wherein the cement powder is arranged in the interior of the cartridge between the delivery opening and the delivery plunger, wherein a hollow cylinder is arranged at a front side of the delivery plunger facing the delivery opening, wherein the hollow cylinder is open at a front face facing the delivery opening and extends from the front side of the delivery plunger at least 3 mm into the interior of the cartridge.

One embodiment provides the delivery plunger tight or sealed relative to an internal wall of the interior of the cartridge, for example, is sealed with at least one circumferential seal.

In one embodiment, the device is also provided for storing the cement powder and in one embodiment also for storing the monomer liquid.

It may be provided that the delivery opening is arranged in the front side of the cartridge. A delivery pipe which defines the delivery opening is or has been in one embodiment arranged at the front side of the cartridge.

The hollow cylinder is arranged in the interior of the cartridge.

The fact that the hollow cylinder extends from the delivery plunger in the direction of a front side of the cartridge and thus in the interior of the cartridge means that a dead volume is defined by the hollow cylinder in the interior of the cartridge. Because a dead volume remains in the interior of the cartridge, a volume may remain between the delivery opening and the delivery plunger which is filled with a mixture of the cement powder and the monomer liquid when the hollow cylinder is pressed against the front side of the interior of the cartridge and the delivery plunger cannot be advanced thereby any further in the direction of the delivery opening.

The cartridge, the delivery plunger and the hollow cylinder are in one embodiment made from a thermoplastic, for example, using an injection molding method.

The interior of the cartridge has a cylindrical geometry. The cylindrical shape is the simplest with which the interior of the cartridge may be made. A cylindrical shape should be understood geometrically to mean the shape of a general cylinder with any desired base area, that is, not just a cylinder with a circular base area. The internal wall of the interior of the cartridge may thus be formed by the cylinder envelope of a cylinder with any desired base area, for example, with different base areas, that is, also with base areas which are not circular or round. According to one embodiment, however, a cylindrical geometry with a rotationally symmetrical and for example, circular base area is in one embodiment for the interior, since this is the easiest to manufacture.

The front side of the delivery plunger is in one embodiment planar apart from the hollow cylinder.

In devices according to one embodiment, it may be provided that the hollow cylinder is spaced at its external circumferential surface at most by 0.5 mm from an internal wall of the interior of the cartridge, in one embodiment at most 0.1 mm from the internal wall of the interior of the cartridge.

This ensures that no or only a little cement powder, which is hard for the monomer liquid to reach and which would impede movement of the delivery plunger, is located between the internal wall of the interior of the cartridge and the external circumferential surface of the hollow cylinder.

It may also be provided that the hollow cylinder rests at least in places against an internal wall of the interior of the cartridge, in one embodiment with its external circumferential surface against the internal wall of the interior of the cartridge.

This ensures that no cement powder, which is hard for the monomer liquid to reach and which would impede movement of the delivery plunger, is located between the internal wall of the interior of the cartridge and the external circumferential surface of the hollow cylinder.

It may furthermore be provided that the hollow cylinder blocks further movement of the delivery plunger in the direction of the front side of the cartridge when the front face of the hollow cylinder rests against the front side of the interior of the cartridge, such that the delivery plunger is spaced from the front side of the interior of the cartridge and a dead volume remains in the interior of the cartridge.

It is thus ensured that the dead volume enclosed in the hollow cylinder retains in the cartridge a remnant of the bone cement paste produced which is less well mixed or which has a variable consistency due to monomer liquid continuing to flow into the interior of the cartridge at the end of the expulsion process.

It may furthermore be provided that the hollow cylinder has at least one slot, in one embodiment at least one slot extending parallel to the cylinder axis of the hollow cylinder, in one embodiment at least one slot reaching from the front side to the delivery plunger.

In this way, the fit of the hollow cylinder may be more readily adapted to the internal wall of the cartridge and the risk of movement of the delivery plunger being blocked with the hollow cylinder is reduced. As an alternative to a course parallel to the cylinder axis of the hollow cylinder, the at least one slot may also run in the form of a spiral in a wall of the hollow cylinder.

It may also be provided that at least one connection is provided in the delivery plunger from the back side of the delivery plunger to the front side of the delivery plunger for introducing the monomer liquid into the interior of the cartridge, wherein the at least one connection is permeable to the monomer liquid and gases and impermeable to the cement powder and wherein the at least one connection leads from the delivery plunger inside the hollow cylinder or through lines in the hollow cylinder at the front face of the hollow cylinder into the interior of the cartridge.

In this way, the monomer liquid, when passed through the feed-through and, inside the hollow cylinder, into the cement powder, has firstly to flow through the cement powder inside the hollow cylinder and cannot flow past the cement powder at the internal wall of the cartridge and so arrive at the delivery opening. When the monomer liquid is passed through the lines in the hollow cylinder into the interior of the cartridge, it flows in a region closer to the middle of the interior of the cartridge, such that the monomer liquid may spread from there also in the direction of the delivery plunger and become better distributed. The mouth of the lines leading into the interior of the cartridge is in one embodiment located in the region of the inner circumferential surface of the hollow cylinder. In this way, it is ensured that the monomer liquid cannot flow along the shortest path to the internal wall of the interior of the cartridge. All of these measures serve to ensure that the bone cement paste produced and the bone cement paste delivered from the device is more homogeneous and no or as little as possible of the monomer liquid becomes entrapped in the bone cement paste.

One further development of one embodiment proposes that cement powder is contained, for example, pressed in, in the part of the interior of the cartridge enclosed by the hollow cylinder.

This makes it clear that a dead volume is to be formed for the bone cement paste in the part enclosed by the hollow cylinder and nothing else is located therein.

One embodiment may be provided that the part of the interior of the cartridge defined by the hollow cylinder is at least 1 cm$^3$ in size, in one embodiment at least 3 cm$^3$ in size.

In this way it is ensured that the enclosed dead volume is sufficiently large to accommodate the residual quantity of bone cement paste of varying consistency arising at the end of the mixing process, without this being able to be delivered and applied using the device. These dead volumes are sufficient to retain in the interior of the cartridge incompletely mixed proportions of the bone cement paste which may arise in the interior of the cartridge in the region of the delivery plunger. It is thereby possible to prevent poorly mixed bone cement paste or a bone cement paste of varying composition and thus consistency, which is unusable, from being delivered at the end of the delivery process.

According to one embodiment, it may be provided that the hollow cylinder extends from the front side of the delivery plunger at least 5 mm into the interior of the cartridge, in one embodiment at least 7.5 mm into the interior of the cartridge, in one embodiment at least 10 mm into the interior of the cartridge.

Thus, on the one hand the dead volume in the region enclosed by the hollow cylinder is increased and on the other hand the distance to the boundary surface between the cement powder and the internal wall of the cartridge is increased which the monomer liquid has to travel through the cement powder before the risk arises of the monomer liquid being able to flow along the internal wall of the cartridge past the cement powder or bone cement paste which has already arisen.

It may furthermore be provided that the wall thickness of the hollow cylinder amounts to at least 1 mm, in one embodiment at least 1.5 mm, in one embodiment at least 2 mm.

This measure also serves to lengthen the distance traveled by the monomer liquid up to the internal wall of the cartridge and thereby to achieve greater homogeneity of the bone cement paste produced. In addition, in this way sufficient stability of the hollow cylinder in one embodiment consisting of plastic is brought about, such that this is not deformed or not excessively deformed at the end of the expulsion process.

Furthermore, in one embodiment, which is also suitable for storing the monomer liquid and thus provides a full-prepacked system, it may be provided that the device having a receptacle in which the monomer liquid, for example, a monomer liquid container containing the monomer liquid, is contained, wherein a back side of the cartridge is connected with a front side of the receptacle, in one embodiment connected in such a way that the interior of the cartridge is aligned with an interior of the receptacle.

In this way, the device is also suitable for storing the monomer liquid and for mixing the monomer liquid with the cement powder within the device. The device is thus a full-prepacked cementing system. The aligned interiors of the cartridge and the receptacle ensure that firstly the conveying plunger may be moved by a pressure acting on the back side of the conveying plunger and then the conveying plunger may be used to drive the delivery plunger by pushing the conveying plunger together with the delivery plunger further in the direction of the delivery opening.

The receptacle is in one embodiment made from a thermoplastic, for example, using an injection molding method.

In this way, the device may be manufactured inexpensively as a hygienic disposable product.

In devices according to one embodiment in which the monomer liquid is arranged in a monomer liquid container within the device, it may be provided that the monomer liquid container is a glass ampoule, a plastic ampoule, a plastic film ampoule or an aluminum/plastic composite pouch. Such monomer liquid containers may store the monomer liquid for a particularly long time.

In devices with receptacles it may also be provided that an interior of the receptacle and the interior of the cartridge are connected together via a connection which is permeable to the monomer liquid and gases but impermeable to the cement powder.

In this way it is ensured that the cement powder does not penetrate through the connection into the interior of the receptacle, there react prematurely with the monomer liquid and then prevent monomer transfer into the interior of the cartridge. The connection is in one embodiment arranged in the delivery plunger.

It may further be provided that the receptacle has a cylindrical interior in which the monomer liquid, for example, a monomer liquid container containing the monomer liquid, is arranged.

The interior of the receptacle has a cylindrical geometry. Here too, the cylindrical shape is the simplest with which the interior of the receptacle may be made. A cylindrical shape should be understood geometrically to mean the shape of a general cylinder with any desired base area, that is, not just a cylinder with a circular base area.

It may furthermore be provided that a conveying plunger movable in the longitudinal direction of the receptacle is arranged in the receptacle, which conveying plunger is advanceable from a back side of the receptacle in the direction of the front side, wherein the monomer liquid, for example, a monomer liquid container containing the monomer liquid, is arranged between the conveying plunger and the delivery plunger. The back side of the receptacle being opposite the front side of the receptacle.

In this way, a full-prepacked cementing system is provided in which all the parent components of the bone cement paste, namely the monomer liquid and the cement powder, are contained and may also be stored.

The conveying plunger closes the receptacle off liquid-tightly at the back side thereof, apart from any ventilation openings that may be present (see below).

It may in this case be provided that at least one protruding point, edge and/or cutting edge is arranged on the front side of the conveying plunger to break the monomer liquid container.

By applying a defined force at a predetermined, spatially defined location, the pressure at this location may be increased under identical force and in this way defined breaking of the monomer liquid container may be achieved. In this way, the operation of breaking open the monomer liquid container is more reproducible.

In devices according to one embodiment with conveying plungers, it may alternatively or additionally be provided that the monomer liquid container inside the receptacle is to be opened, in one embodiment broken open or torn open, by a movement of the conveying plunger in the direction of the front side of the receptacle.

In this way it is ensured that the monomer liquid container may be opened by the axial linear movement of the conveying plunger. An expulsion device with just one rod as axial linear drive may thereby be used both to open the monomer liquid container and to press the monomer liquid into the cartridge and also to press the bone cement paste out of the cartridge.

In one further development of one embodiment it may be provided that at least one ventilation opening, which connects the interior of the receptacle with the surrounding environment, is arranged in a wall of the receptacle.

In this way, the interior of the receptacle may be sterilized with a sterilizing gas.

In this case, it may be provided that the at least one ventilation opening is arranged so close to the conveying plunger such that it is closed by a movement of the conveying plunger towards the front side of the receptacle before a monomer liquid container arranged in the receptacle, in which monomer liquid container the monomer liquid is contained, is opened by the movement of the conveying plunger.

In this way, the monomer liquid cannot leak from the interior of the receptacle when the at least one ventilation opening is closed by the conveying plunger moving towards the front side of the receptacle before the monomer liquid container is opened by the movement of the conveying plunger, that is, is for example squashed, shattered or torn open by the conveying plunger in the interior of the receptacle.

It may in one embodiment be provided that the receptacle and the cartridge are formed in one piece by a tubular container.

This structure is the simplest and most inexpensive structure achievable.

It may also be provided that a fastening means for fastening an expulsion device is arranged on a back side of the device, the delivery plunger being pushable by the fastened expulsion device in the direction of the delivery opening.

The device may be connected and fastened therewith to an expulsion device with an advanceable rod.

It may be provided that the cement powder rests against the front side of the delivery plunger, for example, over the whole surface thereof, wherein the cement powder is in one embodiment pressed into the interior of the cartridge.

This prevents relatively large amounts of entrapped gas from remaining in the cartridge, which might lead to entrapped gas in the bone cement paste on mixing of the monomer liquid with the cement powder. This cannot happen with a densely packed or in one embodiment pressed cement powder, since the monomer liquid wets the particles of the cement powder well and the surface tension of the monomer liquid then does not allow any or at least no relevant entrapped gas between the particles of the cement powder.

It may moreover be provided that the delivery opening is closed at a front side thereof with a closure, for example, with a plug, wherein the bone cement paste is expellable out of the cartridge through the delivery opening when the delivery opening is open, and wherein the closure is in one embodiment permeable to gases and impermeable to the cement powder.

In this way, the cartridge may be readily used to store the cement powder. The closure may be opened. The interior of the cartridge and the cement powder may be sterilized by evacuation and flushing of the interior of the cartridge with a sterilizing gas, such as ethylene oxide, through the closure if the latter is permeable to gases and impermeable to the cement powder.

The closure is in one embodiment a filter, for example, a porous filter, permeable to gases and impermeable to the cement powder.

In devices with a closure it may be provided that the closure has an indentation at a back side facing the interior of the cartridge, in which indentation the frontmost part of the cement powder is contained.

In this way it is achieved that the front part of the bone cement paste, which is contained in the indentation, may be removed with the closure. The monomer liquid arrives in this part last when pressed in from the back side into the cement powder. In this way, a less thoroughly mixed part of the bone cement paste may thus be removed with the closure.

The closure in one embodiment forms with the delivery plunger a cartridge closure system openable by axial pressure acting on the delivery plunger in the direction of the delivery opening.

It may moreover be provided that a delivery pipe is arranged on the front side of the cartridge, wherein the bone cement paste is expellable through the delivery pipe.

In this way, the device may be readily used for application of bone cement paste to locations which are difficult to access.

It may to this end also be provided that the volume of the interspaces between the cement particles of the cement powder in the interior of the cartridge is in the range from 22 percent by volume to 40 percent by volume relative to the total volume of the cement powder. The total volume of the cement powder in one embodiment corresponds to the volume of the interior of the cartridge, which is defined by the delivery plunger and by a closure in a delivery opening at the front side of the cartridge.

Devices according to one embodiment may also be distinguished in that a cross-section area of the interior of the cartridge amounts to at most 16 $cm^2$, in one embodiment at most 5 $cm^2$.

It may likewise also be provided that the internal diameter of the cartridge is smaller than 50 mm, in one embodiment smaller than 20 mm.

The small internal diameter makes the cross-section area of the interior of the cartridge so small that the viscous bone cement paste may be expelled from the cartridge with the assistance of a manually driven expulsion device even if further flow-impeding lines, such as a hose, an applicator tube or a static mixer, are provided in the direction of flow of the bone cement paste.

It may further be provided that the volume of the monomer liquid in the device, for example, of the monomer liquid in a monomer liquid container in the device, is at least as great as the volume of the air-filled interspaces between the cement powder particles in the cartridge, in one embodiment at least as great as the volume of the liquid lines between the interior of the cartridge and the interior of a receptacle in which the monomer liquid is contained plus the volume of the air-filled interspaces between the cement powder particles in the cartridge.

In this way, it may be ensured that the entire cement powder of the monomer liquid may be wetted and a homogeneous bone cement paste thereby produced.

It may further be provided that the hollow cylinder is formed in one piece with the delivery plunger or with a part of the delivery plunger resting against the internal wall of the cartridge.

In this way, the hollow cylinder and the delivery plunger are used as a one-piece component, so reducing production costs. The parts of the device (cartridge, hollow cylinder, delivery plunger) may be produced from plastic by injection molding.

The objects addressed by various embodiments are also achieved by a method for producing a bone cement paste, for example, a pasty polymethyl methacrylate bone cement paste, wherein the bone cement paste is produced from a cement powder and a monomer liquid using a device according to any one of the preceding claims, characterized by the following succession of steps:

a) inserting the device into an expulsion device, the expulsion device having an axially advanceable rod, and pushing the monomer liquid into the interior of the cartridge, such that the monomer liquid mixes with the cement powder, wherein the monomer liquid flows around the hollow cylinder before arriving at the internal wall of the cartridge, b) the delivery plunger is advanced with the rod in the direction of the delivery opening of the cartridge, wherein the mixture consisting of the cement powder and the monomer liquid from the cartridge is discharged from the device as bone cement paste by the movement of the delivery plunger, and c) the front face of the hollow cylinder meets with the front side of the interior of the cartridge, wherein further movement of the delivery plunger in the direction of the delivery opening is blocked with the hollow cylinder and a residual quantity of the mixture of the cement powder with the monomer liquid remains in a part of the interior of the cartridge defined by the hollow cylinder.

It may here be provided that in step a) the monomer liquid is pressed through at least one connection in the delivery plunger impermeable to the cement powder but permeable to gases and the monomer liquid into the cartridge or is pressed through the connection and at least one line in the hollow cylinder into the cartridge, in one embodiment is pressed into the cartridge by movement of a conveying plunger which is driven with the rod of the expulsion device.

In this way, it is ensured that the direction of flow of the monomer liquid has the same direction as the movement of the delivery plunger with which the bone cement paste is discharged from the cartridge. This has the advantage that a single, unidirectional drive may be used both to press in the monomer liquid and to expel the bone cement paste. In this way, conventional expulsion devices such as manually driven cartridge guns may be used for the method according to one embodiment.

It may further be provided that in step a) first of all the device is inserted into the expulsion device, then a conveying plunger, which is mounted movably inside a receptacle arranged on the back side of the cartridge at the back side of the receptacle, is advanced with the rod in the direction of the cartridge, wherein through movement of the conveying plunger a monomer liquid container, in which the monomer liquid is contained, is opened and the monomer liquid is pressed out of the receptacle into the cartridge, wherein the cement powder mixes with the monomer liquid in the interior of the cartridge.

In this way, the method is also suitable for previous storage of the parent components. The method may thereby be used at any time using a compact full-prepacked cementing system.

In this case, it may be provided that, on advance of the conveying plunger, the broken or slit-open or burst-open monomer liquid container is pushed together and at the same time gas is pushed from the receptacle through a connection into the cartridge and is pushed outwards through the cement powder in the cartridge.

Moreover, it may be provided that in step b) a closure, for example, a porous filter, in a delivery opening at the front side of the cartridge is moved or pushed out by the pressure acting on the mixture of the cement powder with the monomer liquid, wherein in one embodiment the closure is then removed from the delivery opening and in one embodiment an application tube or a delivery pipe extension is thereafter fastened to the front side of the cartridge.

This may prevent the cement powder contained in the cartridge from being able to trickle out of the cartridge or the powder from becoming contaminated from outside. At the same time, the content of the cartridge may be sterilized with a sterilizing gas, such as ethylene oxide.

One embodiment is based on the surprising findings that it is possible, with the hollow cylinder at the front side of the delivery plunger, to guide or to allow the monomer liquid to flow, on pressing into the cement powder in the interior of the cartridge, over a greater distance through the cement powder before the monomer liquid reaches the internal wall of the cartridge, and that the formation of monomer liquid bubbles or entrapped monomer liquid in the bone cement paste formed may thereby be prevented or reduced. In this way, a more homogeneous bone cement paste is produced. It has furthermore been found that it is possible, by retaining in the interior of the cartridge a small remnant of the mixture of the cement powder with the monomer liquid arising in the cartridge, for no bone cement paste of a different consistency to be delivered at the end of the expulsion process, since the residual bone cement paste is retained in the cartridge and the delivery opening is closed.

The device according to one embodiment, in its further development as a full-prepacked cementing system, has the significant advantages that the two parent components of the bone cement paste are stored in the closed cementing system and that mixing of the parent components proceeds in the closed device. This means that the device does not have to be filled by the user. The medical user has no contact with the individual parent components of the bone cement. Odor nuisance thereby remains minimal. An advantage of the device in one embodiment also consists in the fact that the monomer liquid is pressed into the cement powder simply by moving forwards a rod of a manually driven expulsion device. In this case, the air present between the cement powder particles is displaced by the monomer liquid. A homogeneous bone cement paste arises without any need for manual mixing with mixing rods with mixing blades. This means that error-prone manual mixing is no longer necessary. Operation of the device is simplified to the greatest possible extent. The system is a ready-to-use system.

The advantages of devices and methods according to various embodiments are based fundamentally on the fact that the per se known linear forward movement of rods of manually operated expulsion devices is exploited in such a way that, through continuous action of the force of the linear forward movement of the rod, firstly a monomer liquid container is opened, the monomer liquid container is then compressed, whereby the monomer liquid exits from the monomer liquid container and is pressed into compacted cement powder, wherein the air present between the cement powder particles is displaced by the pressed-in monomer liquid and, after wetting of the cement powder particles by the monomer liquid, a bone cement paste arises. A prerequisite for this is the use of a cement powder which is such that it is very readily wetted by the monomer liquid and can suck up the latter by capillary action.

The device may be used as a hygienic disposable product, since it may be manufactured to a very considerable extent of plastic and because all parts including the interiors and the cement powder are sterilizable by means of ethylene oxide.

The device according to one embodiment is characterized in that the occurrence of monomer bubbles in the expelled cement paste is effectively prevented if a hollow cylinder with an axial height of at least 3.0 mm and a wall thickness of at least 1.0 mm is mounted on the delivery plunger in the direction of the cartridge head or in the direction of the front side of the cartridge. In this way, the monomer liquid is introduced into the cement powder at least over a distance of 4.0 mm inside the hollow cylinder when the monomer liquid at the front side of the delivery plunger inside the hollow cylinder is introduced or pressed into the cement powder in the interior of the cartridge. This effectively prevents parts of the monomer liquid from moving between the cement powder or the cement paste formed and the cartridge wall during pressing-in of the monomer liquid and forming monomer bubbles.

An example of a device according to one embodiment for storing, mixing and delivering polymethyl methacrylate bone cement may for example have:

a) a hollow-cylindrical container with a connecting element arranged at the cartridge end for connection with an expulsion device,
b) a cartridge head, which terminates the hollow-cylindrical container at the front side, wherein a feed-through for accommodating the delivery pipe is arranged as a delivery opening in the cartridge head, and wherein at least one feed-through connects the outside of the cartridge head in gas-permeable manner with the inside of the cartridge head,
c) a delivery pipe,
d) a closure which is axially movable in the cartridge head and is gas-permeable but impermeable to powder particles, wherein the closure has a feed-through which extends from the bottom to the top and is connected at the top in liquid-permeable manner with the delivery pipe,
e) a conveying plunger, which is arranged axially movably in the container and which closes cartridge bottom in liquid-impermeable manner,
f) a delivery plunger, which is arranged in the container so as to be axially movable between the closure and the conveying plunger, wherein the delivery plunger has at least one liquid-permeable and powder particle-impermeable connection between the two end faces,
g) at least one monomer liquid container, which is arranged in the container between the delivery plunger and the conveying plunger,
h) an interior (the interior of the cartridge), in which the cement powder is arranged, wherein the interior is defined by the internal wall of the container, the closure and the delivery plunger, wherein
i) a hollow cylinder, whose outer circumferential surface rests against the cartridge internal wall, is arranged on the delivery plunger at the end face facing the cartridge head, wherein the hollow cylinder has a height of at least 3.0 mm, in one embodiment of at least 5.0 mm, in the axial direction and a wall thickness of at least 1.0 mm.

The container in this case includes the cartridge as the front part of the container, in which the cement powder is arranged, and a receptacle as the rear part of the container, in which the monomer liquid container is arranged.

A method according to one embodiment, having the following successive steps, may for example be implemented using the exemplary device for mixing the cement powder with the monomer liquid, forming bone cement paste:

a) connecting the expulsion device with the connecting element of the container,
b) advancing the rod of the expulsion device,
c) displacing the conveying plunger in the direction of the cartridge head,
d) compressing the at least one monomer liquid container between the delivery plunger and the conveying plunger,
e) bursting or tearing the monomer liquid container,
f) pushing together the burst or torn monomer liquid container and expelling the air from the interior of the receptacle and the monomer liquid with the conveying plunger through the at least one connection of the delivery plunger into the cement powder in the interior of the cartridge,
g) pushing the monomer liquid container further together and expelling the monomer liquid with the conveying plunger through the liquid-permeable connection in the delivery plunger and introducing the monomer liquid through the hollow cylinder into the cement powder in the interior of the cartridge,
h) dispersing the monomer liquid in the cement powder with simultaneous displacement of the air out of the interspaces between the cement powder particles,
i) wetting the cement powder particles with the monomer liquid,
j) venting the air out of the cement powder through the gas-permeable closure,
k) swelling of the cement powder particles by the monomer liquid and initiation of free-radical polymerization of the monomer liquid by reaction of the accelerator with the initiator,
l) forming the bone cement paste from the cement powder and the monomer liquid,
m) opening the closure in the delivery opening by axial application of pressure by the bone cement paste pressed axially in the direction of the cartridge head,
n) expelling the bone cement paste through the delivery opening as a result of the forward movement of the delivery plunger and of the conveying plunger, and
o) moving the delivery plunger axially in the direction of the cartridge head until the hollow cylinder meets the cartridge head and blocks further movement of the delivery plunger.

When the hollow cylinder blocks further movement of the delivery plunger, a remnant of the mixture or of the bone cement paste is left in the space defined by the hollow cylinder in the interior of the cartridge.

An exemplary variant of the method is characterized by the following steps after step l) of the above-described method:

l1) expelling the closure from the delivery opening, and
l2) dropping the closure out of the delivery opening or a delivery pipe.

Further exemplary embodiments are explained below with reference to nine schematically depicted figures, but without thereby restricting the invention.

FIGS. 1 to 9 illustrate illustrations of a device according to embodiments. FIGS. 1 to 3 and 5 and 6 illustrate different schematic overall views of the exemplary device according to one embodiment. FIGS. 4 and 7 to 9 illustrate schematic cross-sectional views as detail views, in the form of enlarged details, through different regions of the device according to one embodiment.

The device according to one embodiment consists substantially of a tubular container of plastic, which forms as the front part (at the top in FIGS. 1 and 2, to the left in FIGS. 3, 4 and 7 to 9, top right in FIG. 5 and bottom left in FIG. 6) a cartridge 1 with a cylindrical interior and which forms as the rear part a receptacle 2 for a glass ampoule 3 as monomer liquid container. Instead of the glass ampoule 3, a break-openable plastic ampoule may also straightforwardly be used or, with minor alterations, a tear-openable film pouch consisting of a metal-coated plastic may also be used instead of the glass ampoule 3.

Figure 2:
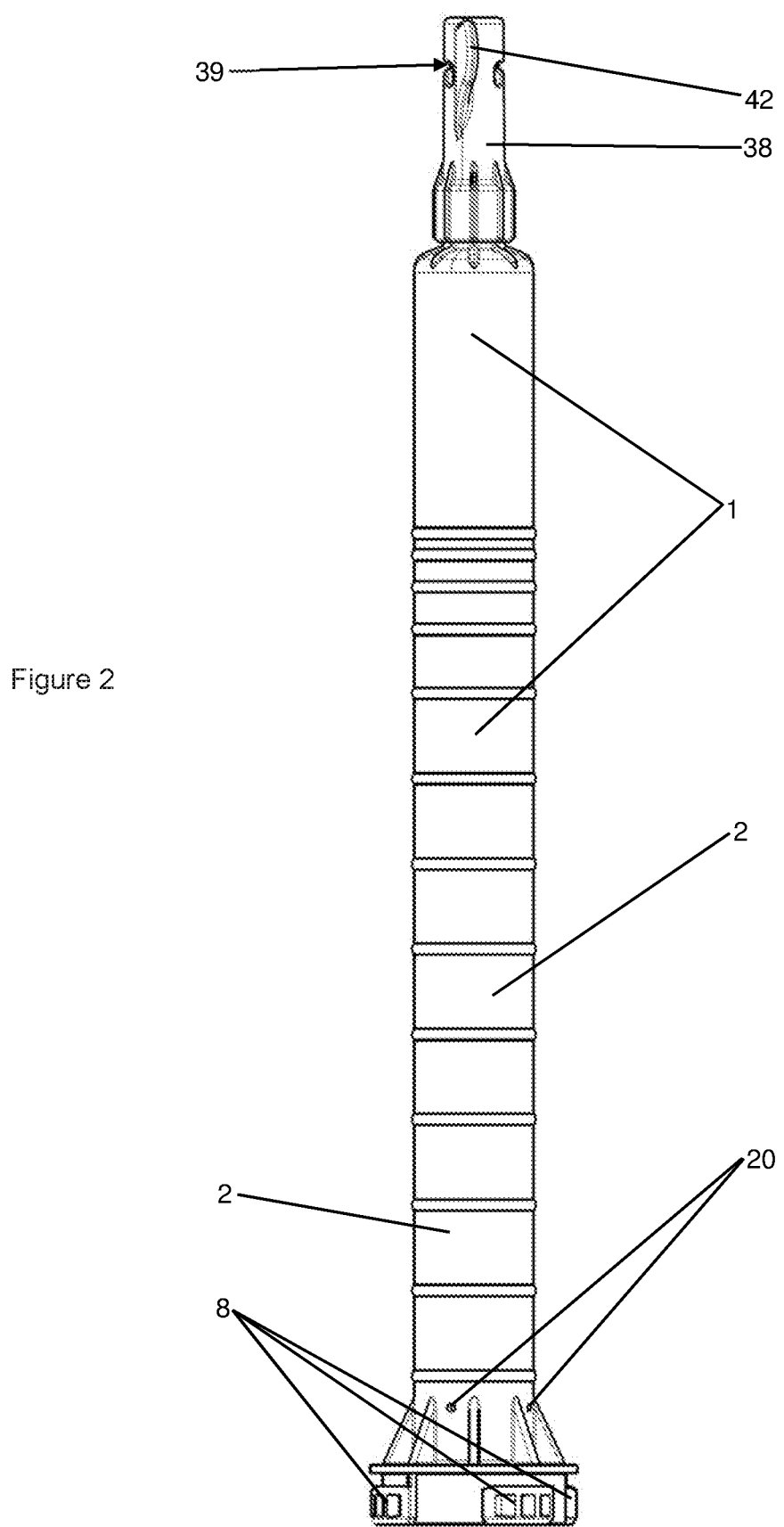
FIG. 2 illustrates a schematic side view of the device according to FIG. 1.
Figure 3:
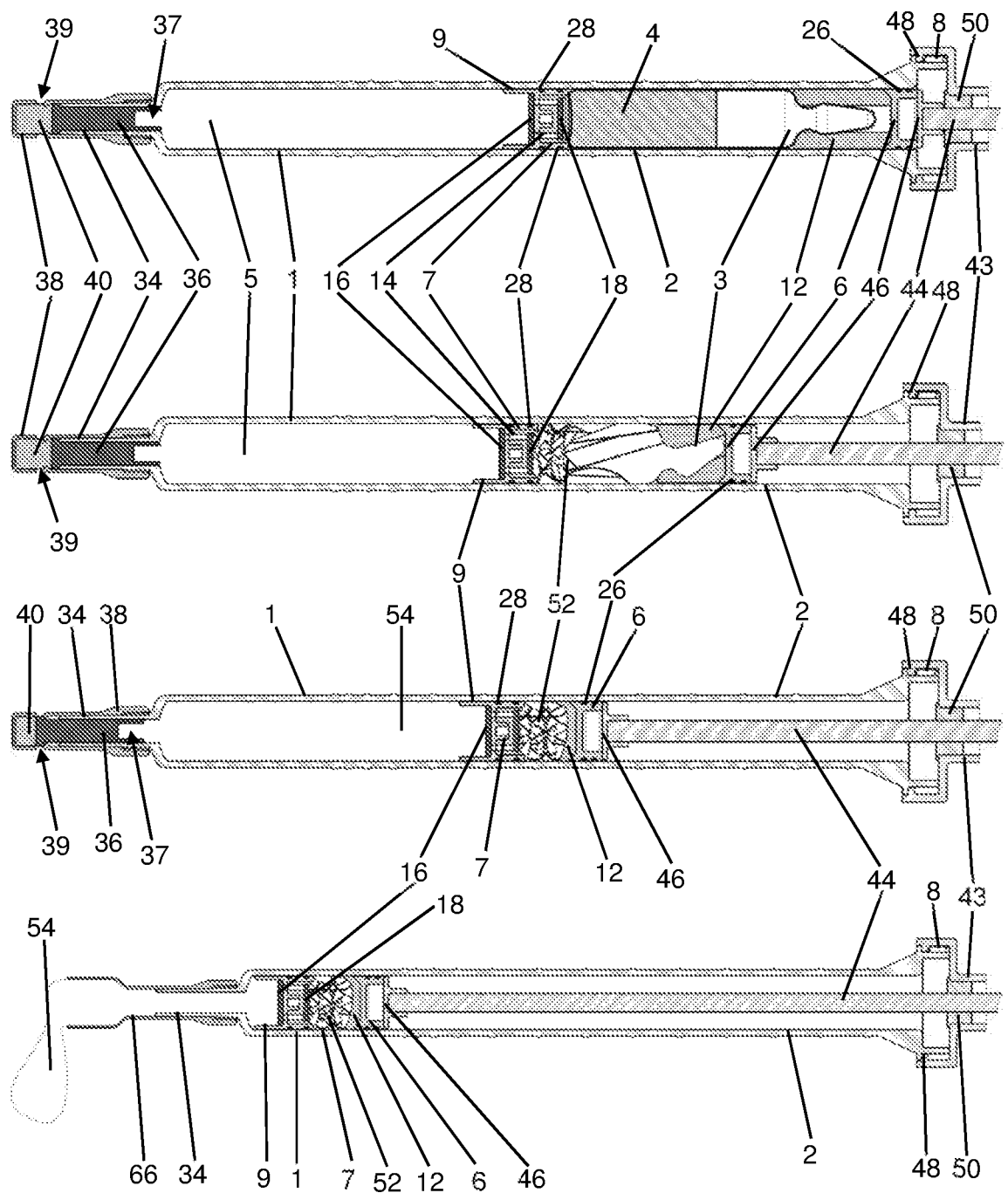
FIG. 3 illustrates four schematic cross-sectional views one above the other of the device according to FIGS. 1 and 2 with a connected expulsion device to illustrate the sequence of a method according to one embodiment.
Figure 5:
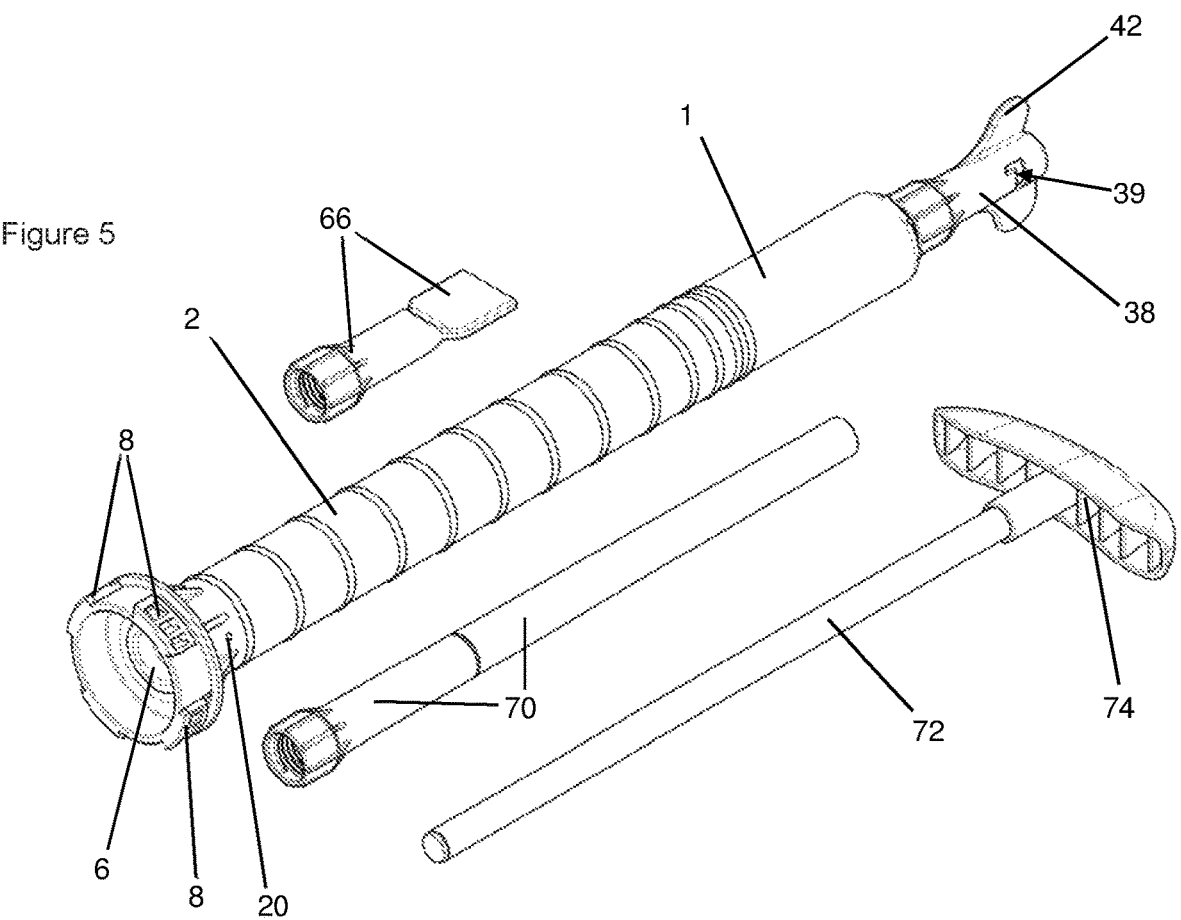
FIG. 5 illustrates a schematic perspective view of the parts of a device according to one embodiment with application tube and a delivery pipe extension.
Figure 6:
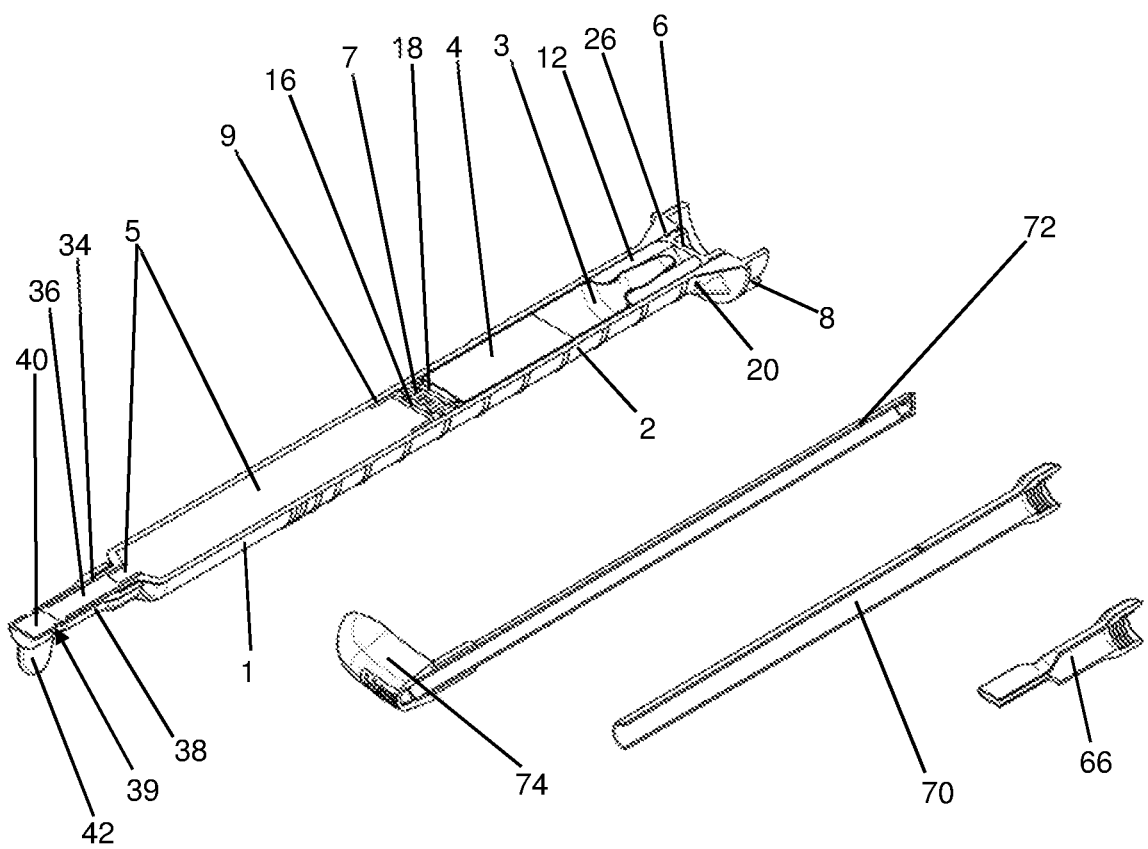
FIG. 6 illustrates a schematic perspective cross-sectional view of the device with the application tube and the delivery pipe extension according to FIG. 5.
Figure 7:
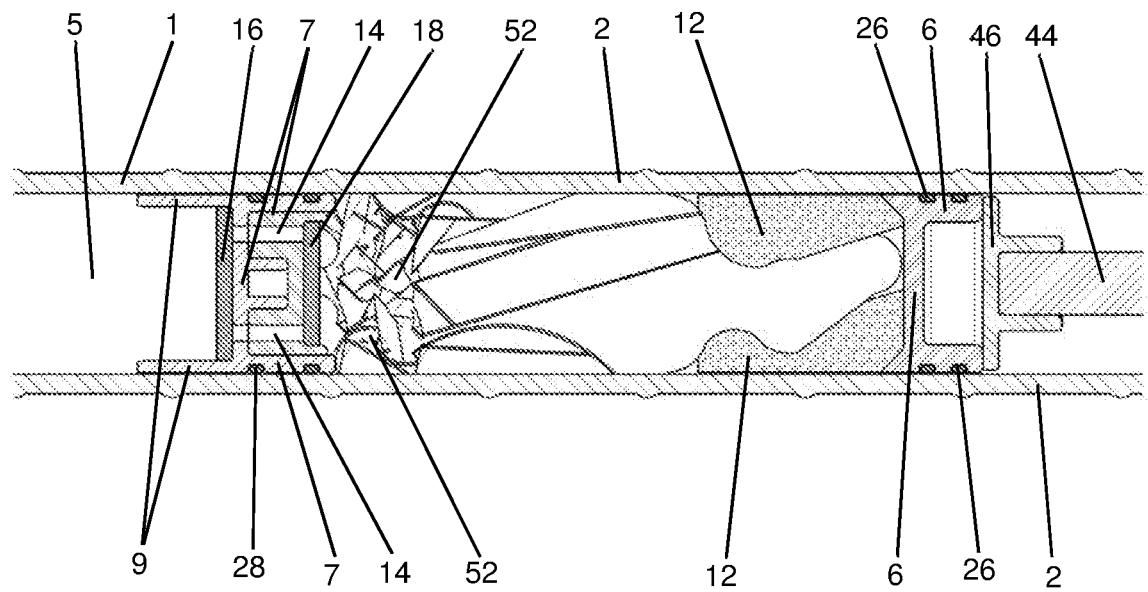
FIG. 7 illustrates a schematic cross-sectional view in the form of an enlarged detail of the device according to the second illustration from the top of FIG. 3 during pressing in of the monomer liquid.
Figure 8:
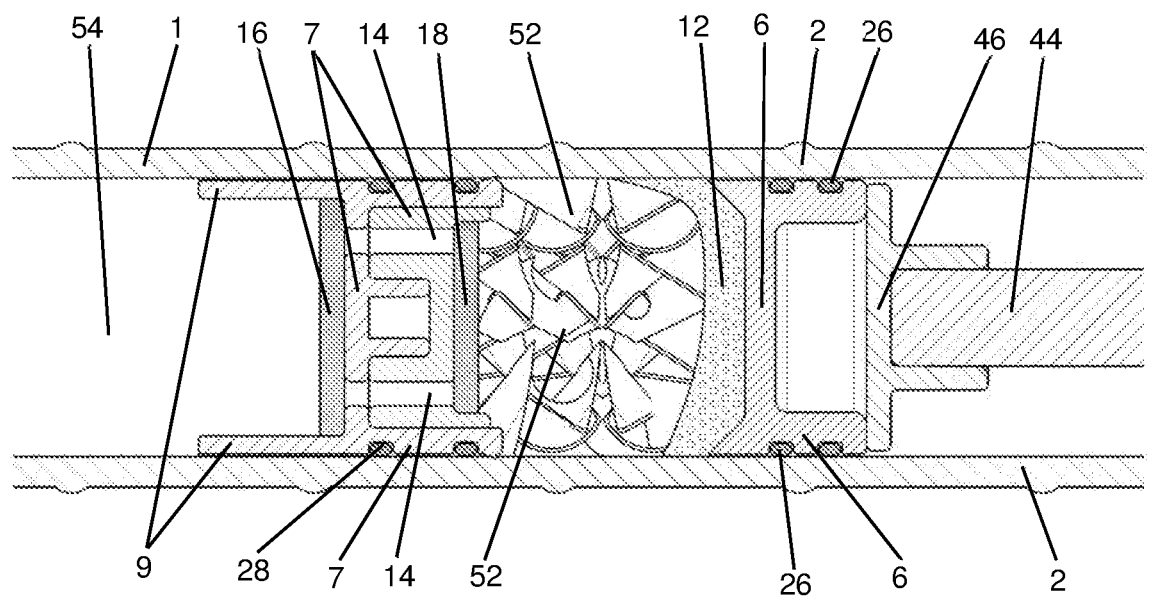
FIG. 8 illustrates a schematic cross-sectional view in the form of an enlarged detail of the device according to the third illustration from the top of FIG. 3 during pressing forward of the bone cement paste.
Figure 9:
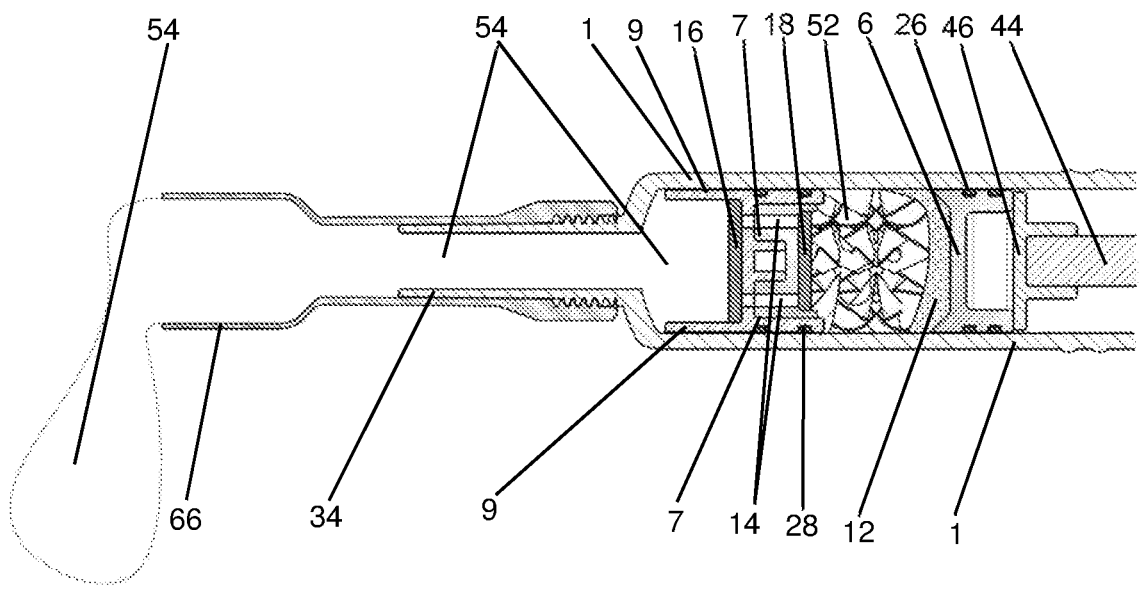
FIG. 9 illustrates a schematic cross-sectional view in the form of an enlarged detail of the device according to the last illustration from the top of FIG. 3 during delivery of the bone cement paste.

The back side of the device is at the bottom in FIGS. 1 and 2, to the right in the illustrations of FIG. 3, bottom left in FIG. 5 and top right in FIG. 6. The tubular shape of the container is particularly apparent in the cross-sectional views of FIGS. 1, 3 and 6. Both the interior of the cartridge 1 and the interior of the receptacle 2 are cylindrical with a circular base area. In this respect, the diameter of the interior of the cartridge 1 and the diameter of the interior of the receptacle 2 are identical in size and aligned. The container with the receptacle 2 and the cartridge 1 is in one embodiment produced from plastic using injection molding technology. The receptacle 2 thus has a cylindrical interior, into which the glass ampoule 3 has been placed. The glass ampoule 3 contains the monomer liquid 4. In FIG. 1 the device is illustrated turned upside-down, such that gravity works upwards and the monomer liquid 4 collects in the upper part of the glass ampoule 3. A cement powder 5 has been poured or in one embodiment pressed into the interior of the cartridge 1. The monomer liquid 4 and the cement powder 5 form the parent components for a PMMA bone cement, which can be produced using the device. Owing to the glass ampoule 3, the monomer liquid 4 can be stored for a very long time in the receptacle 2 and thereby in the device. The cement powder 5 can likewise be stored for extended periods in the device. The device is thus suitable for storing the monomer liquid 4 and the cement powder 5 as parent components of a bone cement paste of the PMMA bone cement. The device is, however, also suitable and provided for mixing the bone cement paste from the parent components and for delivering the mixed bone cement paste.

Arranged in the receptacle 2 is a conveying plunger 6 of plastic movable in the longitudinal direction in the cylindrical interior of the receptacle 2. The conveying plunger 6 is arranged in the region of the back side of the receptacle 2. The glass ampoule 3 may be compressed, and shattered in the process, in the receptacle 2 using the conveying plunger 6, in that the conveying plunger 6 is pushed in the direction of the front side, that is, in the direction of the cartridge 1. The conveying plunger 6 has wipers at the front side with which splinters of the glass ampoule 3 are wiped off the internal wall of the receptacle 2. To this end, the wipers rest laterally against the internal wall of the interior of the receptacle 2.

A delivery plunger 7 of plastic is arranged in the interior of the cartridge 1, at the back side thereof (towards the bottom in FIGS. 1 and 2, to the right in FIGS. 3, 4 and 7 to 9). At the back side of the receptacle 2 a fastening means 8 is provided, with which the receptacle 2 may be connected to an expulsion device 43 (not visible in FIGS. 1 and 2 but see FIG. 3). The fastening means 8 is in one embodiment suitable and provided for forming a bayonet closure 8. The conveying plunger 6, which is freely accessible from the back side of the receptacle 2, can thereby be advanced with the expulsion device 43 in the direction of a front side of the cartridge 1.

At its front side, the delivery plunger 7 has a hollow cylinder 9 for extending the distance over which the monomer liquid 4 must flow through the cement powder 5 until it reaches the internal wall of the cartridge 1. In addition, the hollow cylinder 9 serves to space the delivery plunger 7 from a delivery opening at the front side of the interior of the cartridge 1 and to create a dead volume between the delivery plunger 7 and the front side of the interior of the cartridge 1 when the delivery plunger 7 or the hollow cylinder 9 is pushed to the greatest possible extent against the front side of the interior of the cartridge 1. In the present case, the hollow cylinder 9 is rotationally symmetrical and is shaped in the manner of a tube section. The hollow cylinder 9 may, however, also have longitudinal cuts extending parallel to the cylinder axis of the hollow cylinder 9. At the front side the hollow cylinder 9 is planar. The hollow cylinder 9 is open at a front face facing the delivery opening.

In the interior of the receptacle 2 a bearing 12 of foam is provided which serves as a transport safeguard and as an impact safeguard for the glass ampoule 3. In this way it is intended to prevent the glass ampoule 3 from breaking open unintentionally in the event of vibrations or impacts. The foam and thus the bearing 12 are gas-permeable.

The cartridge 1 and the receptacle 2 are embodied in one piece as a joint plastics part. The receptacle 2 and the cartridge 1 are connected together via a connection 14 in the delivery plunger 7 in a liquid-permeable manner for the monomer liquid 4. The connection 14 through the delivery plunger 7 leads through a porous filter 16 impermeable to the cement powder 5 but permeable to the monomer liquid 4 into the interior of the cartridge 1.

At the mouth leading to the connection 14 a filter 18 is arranged in the delivery plunger 7, with which filter the splinters of the glass ampoule 3 can be held back. A screen may also be provided instead of the filter 18 or in addition to the filter 18.

A plurality of ventilation openings 20 are provided in the wall of the receptacle 2, through which the interior of the receptacle 2 may be sterilized by means of a sterilizing gas such as ethylene oxide. The bearing 12 is likewise gas-permeable and therefore does not close the ventilation openings 20. The ventilation openings 20 are arranged directly adjacent the conveying plunger 6, such that the conveying plunger 6 is pushed directly in front of the ventilation openings 20 and thus directly closes the ventilation openings 20 when the conveying plunger 6 is advanced in the direction of the cartridge 1. This prevents monomer liquid 4 from being able to escape through the ventilation openings 20 when the glass ampoule 3 in the receptacle 2 has been opened.

The cylindrical conveying plunger 6 has an outer circumference which matches the cylindrical geometry of the interior of the receptacle 2 and is sealed in liquid-tight manner relative to the internal wall of the receptacle 2 via two circumferential seals 26. The delivery plunger 7 is likewise sealed in liquid-tight manner relative to the internal wall of the cartridge 1 via two circumferential seals 28. These seals 26, 28 serve to prevent monomer liquid 4 or bone cement from escaping, so as to prevent contamination of the surrounding environment (the operating room and the user). To this end, the seals 26, 28 may consist of rubber.

The interior of the cartridge 1 leads at the front side into a delivery pipe 34, which defines the delivery opening of the cartridge 1. The delivery pipe 34 has an outer thread at its base. Inside the delivery pipe 34 a porous filter 36 is arranged as closure for the cartridge 1. The porous filter 34 is impermeable to the cement powder 5 but permeable to gases. An indentation 37 is provided in the back side of the porous filter 36. The cement powder 5 is also contained in the indentation 37. At the outer thread of the delivery pipe 34 a cap 38 is fastened, wherein the front part of the cap 38 is filled with an expanded polystyrene or foam 40. Two wings 42 are provided on the cap 38, such that the cap 38 may be screwed conveniently by hand off the delivery pipe 34 in the manner of a wing screw. The cap 38 has lateral openings 39. As a result of this structure, the interior of the cartridge 1 and the cement powder 5 may be sterilized using ethylene oxide, since the openings 39 in the cap 38, the expanded polystyrene or the foam 40, the porous filter 36 and the interspaces between the powder particles of the cement powder 5 are air-permeable. At the same time, air may be ejected from the receptacle 2 through the cement powder 5, the porous filter 36, the expanded polystyrene or foam 40 and the openings 39 in the cap 38 when the conveying plunger 6 is pressed in the direction of the receptacle 1. The cap 38 forms, together with the expanded polystyrene or foam 40 and with the porous filter 36, a closure for the delivery opening of the cartridge 1 or for the delivery pipe 34.

The cement powder 5 is enclosed in the cartridge 1, since all the openings 39 and connections 14 are closed in a manner impermeable to the cement powder 5 by means of the porous filters 16, 36. The contents of the cartridge 1 may in this respect be sterilized by evacuation and flushing with ethylene oxide. This renders the device also suitable for long-term storage of the cement powder 5.

In addition to the device, FIGS. 5 and 6 also illustrate the application tube 66 and the delivery pipe extension 70 for the device, which may be screwed onto the delivery pipe 34 as respective alternatives instead of the cap 38. To this end, the application tube 66 and the delivery pipe extension 70 have an internal thread matching the outer thread of the delivery pipe 34. The delivery pipe extension 70 may be closed with a closure 72. The closure 72 ends in a handle 74, with which the delivery pipe extension 70 may be readily screwed by hand onto the delivery pipe 34 when the closure 72 is in the delivery pipe extension 70. In addition, the handle 74 may be used readily to remove the closure 72, which closes the side of the delivery pipe extension 70 facing the cartridge 1, even if the delivery pipe extension 70 is firmly screwed together with the delivery pipe 34.

Figure 4:
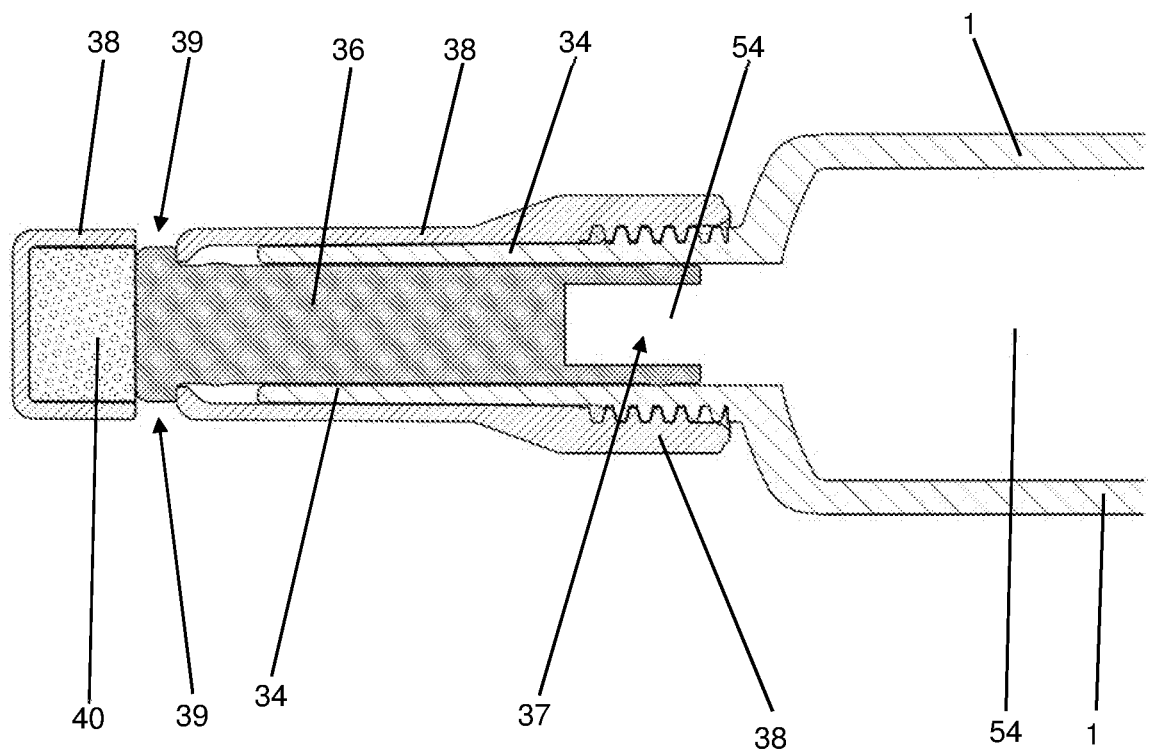
FIG. 4 illustrates a schematic cross-sectional view in the form of an enlarged detail through the front part of the device according to one embodiment according to FIGS. 1 to 3 with advanced porous filter.

FIG. 3 illustrates four schematic cross-sectional views of the device according to one embodiment according to FIGS. 1 and 2, one above the other to illustrate the sequence of a method according to one embodiment. In addition, FIG. 4 illustrates an enlarged detail of the third illustration of FIG. 3, FIG. 7 an enlarged detail of the second illustration from the top of FIG. 3, FIG. 8 an enlarged detail of the fourth illustration from the top of FIG. 3 and FIG. 9 an enlarged detail of the bottommost illustration of FIG. 3.

At the start of the method, the device is in the initial state, as illustrated also in FIG. 1. In this state, the device is inserted into an expulsion device 43, for example a conventional, manually drivable cartridge gun. This situation is illustrated in the topmost illustration of FIG. 3. The expulsion device 43 includes a linearly advanceable rod 44. Only the front part of the expulsion device 43 is depicted. The expulsion device 43 also includes a handle and a rocker arm (not visible in the figures) for manually driving the rod 44 of the expulsion device 43, as is also the case with conventional manually driven expulsion devices. The device is fastened with the fastening means 8 to the expulsion device 43 (see topmost illustration in FIG. 3). A flat disc 46 is provided at the tip of the rod 44 to drive the conveying plunger 6. The rod 44 pushes on the conveying plunger 6 with the disc 46 when the rod 44 of the expulsion device 43 is pushed into the receptacle 2. The expulsion device 43 is to this end connected via a mating fastening means 48 to the back side of the receptacle 2, such that the disc 46 pushes on the conveying plunger 6 on advance of the rod 44 and advances it in the direction of the cartridge 1. To this end, the rod 44 is mounted so as to be linearly mobile relative to a bearing 50 and thereby relative to the mating fastening means 48 and thus relative to the receptacle 2.

The expulsion device 43 is operated and in the process the rod 44 and, with the rod 44, the conveying plunger 6 is advanced in the direction of the cartridge 1. At the start of the movement of the conveying plunger 6, the latter closes the ventilation openings 20. The bearing 12 is compressed and the conveying plunger 6 meets the head of the glass ampoule 3. Since the glass ampoule 3 rests at the front side against the delivery plunger 7 and the interior of the receptacle 2 becomes increasingly smaller, the glass ampoule 3 is broken. The monomer liquid 4 exits from the glass ampoule 3 into the interior of the receptacle 2. The delivery plunger 7 cannot be pushed or cannot be pushed far by the glass ampoule 3 in the direction of the porous filter 36 when the cement powder 5 is dry, that is, has not been wetted by the monomer liquid 4, since the dry cement powder 5 is not flowable and blocks movement of the delivery plunger 7. This situation is illustrated in FIG. 3, second illustration from the top, and in the enlarged detail view in FIG. 7. Residual air from the receptacle 2 is forced out of the device through the filter 18, the connection 14, the porous filter 16, through the interspaces between the particles of the cement powder 5, through the porous filter 36, through the foam 40 and out of the openings 39 in the cap 38.

Ultimately, all that remains of the glass ampoule 3 is small splinters 52, which are retained by the filter 18 and remain in the tubular container. The monomer liquid 4 is pressed through the filter 18, the connection 14 and the porous filter 16 into the cement powder 5 and there begins to react with the cement powder 5, such that the bone cement paste 54 forms from the mixture 54. In this case, the monomer liquid 4 cannot flow directly out of the porous filter 16 to the internal wall of the cartridge 1, since this is completely or, in the case of a slotted hollow cylinder 9, largely concealed by the hollow cylinder 9. In this way, the monomer liquid 4 is forced to clear a path through the cement powder 5. Monomer liquid bubbles or monomer liquid accumulations can be prevented in this way and a more homogeneous bone cement paste 54 is mixed than without use of the hollow cylinder 9.

The quantity of monomer liquid 4 is selected such that the cement powder 5 is wetted with the monomer liquid 4 up to the frontmost point of the cartridge 1, that is, as far as into the indentation 37 in the porous filter 36. This situation is illustrated in FIG. 3, third illustration from the top and in the detail view according to FIG. 8. As soon as the mixture 54 has arisen, the porous filter 36 is driven forwards by the pressure acting on the mixture 54 due to the pressure on the delivery plunger 7 and compresses the foam 40. When the porous filter 36 then slides forwards, it becomes visible to the user from outside through the opening 39 in the cap 38. This situation is illustrated in detail in FIG. 4. To this end, the porous filter 36 in one embodiment has a different color and/or brightness from the foam 40. For example, the foam 40 may be white and the porous filter 36 red.

In this state the cap 38 is screwed off with the porous filter 36 and the foam 40 and an extended delivery opening in the form of an applicator tube 66 or in the form of a delivery pipe extension 70 is screwed onto the delivery pipe 34 instead (see also FIG. 5 and FIG. 6). When the cap 38 is screwed off, the frontmost part of the mixture 54 or of the bone cement paste 54, which is located in the indentation 37 of the porous filter 38, is removed with the cap 38 and the porous filter 36. In this way, a potentially less well mixed part of the bone cement paste 54 is removed and thus greater homogeneity of the available bone cement paste 54 is achieved.

By advancing the rod 44 further, the conveying plunger 6, the broken glass 52 and the delivery plunger 7 arranged in front thereof are driven. The bone cement paste 54 is then delivered from the cartridge 1 via the applicator tube 66. To this end, the delivery plunger 7 is advanced with the rod 44 in the direction of the delivery pipe 34 (see in this respect also the fourth illustration from the top in FIG. 3 and the detail view according to FIG. 9). The bone cement paste 54 is discharged from the interior of the cartridge 1 through the delivery pipe 34 and the applicator tube 66 and may be applied there or theoretically used for further processing.

Finally, the hollow cylinder 9 meets with the cartridge head or the front side of the interior of the cartridge 1. Since the delivery plunger 7 is blocked at the end of the expulsion process, it may happen that the broken glass and splinters 52 from the glass ampoule 3 are compressed still further by the increasing pressure acting on the broken glass and splinters 52 and in the process yet further remnants of the monomer liquid 4 are forced out of the interspace between the delivery plunger 7 and the conveying plunger 6 into the front part of the cartridge 1. This may result in a change in the composition of the bone cement paste 54, since the proportion of liquid monomer liquid 4 in the mixture 54 is increased. When the bone cement paste 54 has already very largely reacted, it may also happen that the monomer liquid 4 forces its way past the bone cement paste 54. The hollow cylinder 9 has a height of 3 mm, in one embodiment of 5 mm or greater, such that it is ensured by the distance created thereby that the front side of the delivery plunger 7 is spaced from the front side of the interior of the cartridge 1 when the delivery plunger 7 has been forced as far forwards as is possible with a manually driven expulsion device 43. This creates a dead volume in the interior of the cartridge 1, and specifically in the region defined by the hollow cylinder 9, which cannot be discharged from the cartridge 1 through the delivery opening and the delivery pipe 34.

The part of the bone cement paste 54 which optionally contains too great a proportion of monomer liquid 4 is now located in this dead volume. Even if more pressure subsequently continues to be applied, no further bone cement paste 54 can be expelled out of the device from the dead volume. This structure ensures that no bone cement paste 54 of variable consistency due to a variable composition can be applied with the device.

The openings 39 also serve as a visual marker by means of which it can be identified when the device is ready to use. When the porous filter 36 is pushed forwards due to the pressure of the bone cement paste 54 and in the process compresses the expanded polystyrene 40 in the cap 38, the porous filter 36 becomes visible through the openings 39. This allows the user to recognize that the bone cement paste 54 is present in the fully mixed state in the cartridge 1 and thus is ready for use. At this point, the user can unscrew the cap 38 with the porous filter 36 and screw the applicator tube 66 or the delivery pipe extension 70 onto the delivery pipe 34. The delivery plunger 7 may then be driven with the rod 44 via the conveying plunger 6 and the bone cement paste 54 thereby discharged from the cartridge 1 through the applicator tube 66 or the delivery pipe extension 70.

The features of one embodiment disclosed in the above description, as well as in the claims, figures and exemplary embodiments, may be important both individually and in any desired combination to realization of various embodiments.

Although specific embodiments have been illustrated and described herein, it will be appreciated by those of ordinary skill in the art that a variety of alternate and/or equivalent implementations may be substituted for the specific embodiments illustrated and described without departing from the scope of the present embodiments. This application is intended to cover any adaptations or variations of the specific embodiments discussed herein. Therefore, it is intended that these embodiments be limited only by the claims and the equivalents thereof.

What is claimed is:

1. A device for producing a bone cement paste from a monomer liquid and a cement powder as parent components of the bone cement paste and for delivering the mixed bone cement paste, the device comprising:
    a cartridge with a cylindrical interior, wherein the interior of the cartridge is closed at a front side apart from a delivery opening for discharging the bone cement paste, wherein a delivery plunger is arranged in the interior of the cartridge the delivery plunger being pushable in the direction of the delivery opening and wherein the cement powder is arranged in the interior of the cartridge between the delivery opening and the delivery plunger; and
    a receptacle in which the monomer liquid is contained, wherein a back side of the cartridge is connected with a front side of the receptacle, and wherein the receptacle and the cartridge are configured as a one-piece tubular container;
    wherein a hollow cylinder is arranged at a front side of the delivery plunger facing the delivery opening;
    wherein the hollow cylinder is open at a front face facing the delivery opening and extends from the front side of the delivery plunger at least 3 mm into the interior of the cartridge;
    wherein at least one connection is provided in the delivery plunger from the back side of the delivery plunger to the front side of the delivery plunger for introducing the monomer liquid into the interior of the cartridge;
    wherein the at least one connection is permeable to the monomer liquid and gases and at the same time is impermeable to the cement powder; and
    wherein the at least one connection leads from the delivery plunger inside the hollow cylinder or through lines in the hollow cylinder at the front face of the hollow cylinder into the interior of the cartridge.

2. The device of claim 1, characterized in that the hollow cylinder is spaced at its external circumferential surface at most by 0.1 mm from an internal wall of the interior of the cartridge.

3. The device according to claim 1, characterized in that the hollow cylinder rests at least in places against an internal wall of the interior of the cartridge.

4. The device of claim 1, characterized in that the hollow cylinder blocks further movement of the delivery plunger in the direction of a front side of the cartridge when the front face of the hollow cylinder rests against the front side of the interior of the cartridge, such that the delivery plunger is spaced from the front side of the interior of the cartridge and a dead volume remains in the interior of the cartridge.

5. The device of claim 1, characterized in that the hollow cylinder has at least one slot extending parallel to the cylinder axis of the hollow cylinder and reaching from the front side to the delivery plunger.

6. The device of claim 1, characterized in that cement powder is pressed in the part of the interior of the cartridge enclosed by the hollow cylinder.

7. The device of claim 1, characterized in that the part of the interior of the cartridge defined by the hollow cylinder has a volume of at least 3 $cm^3$.

8. The device of claim 1, characterized in that the hollow cylinder extends from the front side of the delivery plunger at least 10 mm into the interior of the cartridge.

9. The device of claim 1, characterized in that the wall thickness of the hollow cylinder amounts to at least 2 mm.

10. The device of claim 1, characterized in that the device having the receptacle in which a monomer liquid container containing the monomer liquid, is contained, wherein the back side of the cartridge is connected with the front side of the receptacle, and connected in such a way that the interior of the cartridge is aligned with an interior of the receptacle.

11. The device according to claim 10, characterized in that an interior of the receptacle and the interior of the cartridge are connected together via a connection which is permeable to the monomer liquid and gases but impermeable to the cement powder.

12. The device of claim 10, characterized in that the receptacle has a cylindrical interior in which a monomer liquid container containing the monomer liquid, is arranged.

13. The device of claim 10, characterized in that a conveying plunger movable in the longitudinal direction of the receptacle is arranged in the receptacle, which conveying plunger is advanceable from a back side of the receptacle opposite the front side of the receptacle in the direction of the front side of the receptacle, wherein a monomer liquid container containing the monomer liquid, is arranged between the conveying plunger and the delivery plunger.

14. The device of claim 10, characterized in that at least one ventilation opening, which connects the interior of the receptacle with the surrounding environment, is arranged in a wall of the receptacle.

15. The device of claim 14, characterized in that the at least one ventilation opening is arranged so close to the conveying plunger such that it is closed by a movement of the conveying plunger in the direction of the front side of the receptacle before the monomer liquid container arranged in the receptacle, in which monomer liquid container the monomer liquid is contained, is opened by the movement of the conveying plunger.

16. The device of claim 1, characterized in that a fastening means for fastening an expulsion device is arranged on a back side of the device, the delivery plunger being pushable by the fastened expulsion device in the direction of the delivery opening.

17. The device of claim 1, characterized in that the delivery opening is closed at a front side thereof with a plug, wherein the bone cement paste is expellable out of the cartridge through the delivery opening when the delivery opening is open, and wherein the plug is permeable to gases and impermeable to the cement powder.

18. The device according to claim 17, characterized in that the plug has an indentation at a back side facing the interior of the cartridge, in which indentation a frontmost part of the cement powder is contained.

19. The device of claim 1, characterized in that a delivery pipe is arranged on the front side of the cartridge, wherein the bone cement paste is expellable through the delivery pipe.

20. The device of claim 1, characterized in that a cross-section area of the interior of the cartridge amounts to at most 5 cm$^2$.

21. The device of claim 1, characterized in that the hollow cylinder is formed in one piece with the delivery plunger or with a part of the delivery plunger resting against the internal wall of the cartridge.

* * * * *